US011033550B2

(12) United States Patent
Kato et al.

(10) Patent No.: US 11,033,550 B2
(45) Date of Patent: Jun. 15, 2021

(54) MEDICAMENT

(71) Applicant: TAKEDA PHARMACEUTICAL COMPANY LIMITED, Osaka (JP)

(72) Inventors: Juran Kato, Kanagawa (JP); Hiroko Yamakawa, Kanagawa (JP); You Muraki, Kanagawa (JP); Gattu Mahanandeeshwar, Hyderabad (IN); Oruganty Satyalakshmi, Mallapur (IN)

(73) Assignee: TAKEDA PHARMACEUTICAL COMPANY LIMITED, Osaka (JP)

( * ) Notice: Subject to any disclaimer, the term of this patent is extended or adjusted under 35 U.S.C. 154(b) by 382 days.

(21) Appl. No.: 16/089,533

(22) PCT Filed: Mar. 27, 2017

(86) PCT No.: PCT/JP2017/012305
§ 371 (c)(1),
(2) Date: Sep. 28, 2018

(87) PCT Pub. No.: WO2017/170354
PCT Pub. Date: Oct. 5, 2017

(65) Prior Publication Data
US 2020/0306249 A1 Oct. 1, 2020

(30) Foreign Application Priority Data
Mar. 28, 2016 (JP) .............................. JP2016-063747

(51) Int. Cl.
*A61K 31/519* (2006.01)
*A61P 9/12* (2006.01)

(52) U.S. Cl.
CPC .............. *A61K 31/519* (2013.01); *A61P 9/12* (2018.01)

(58) Field of Classification Search
CPC ................................ A61K 31/519; A61P 9/12
See application file for complete search history.

(56) References Cited

U.S. PATENT DOCUMENTS

| 7,514,441 | B2 | 4/2009 | Yasuma et al. |
| 9,447,100 | B2 | 9/2016 | Yasuma et al. |
| 2004/0242602 | A1 | 12/2004 | Gungor et al. |
| 2006/0079536 | A1 | 4/2006 | Yasuma et al. |
| 2009/0304821 | A1 | 12/2009 | Notoya et al. |
| 2015/0266872 | A1 | 9/2015 | Koike et al. |

FOREIGN PATENT DOCUMENTS

| CA | 3009609 | A1 | 6/2017 |
| CN | 1771231 | A | 5/2006 |
| CN | 104910118 | A | 9/2015 |
| EP | 3395344 | A1 | 10/2018 |
| JP | 2005-239611 | A | 9/2005 |
| JP | 2006-510582 | A | 3/2006 |
| WO | 2004/017908 | A2 | 3/2004 |
| WO | 2013/113860 | A1 | 8/2013 |
| WO | 2014/061676 | A1 | 4/2014 |
| WO | 2017/110881 | A1 | 10/2018 |

OTHER PUBLICATIONS

Gehlbach et al. (Chest (2004); 125:669-682).*
Dunlap et al. and Korman et al. (2010, 2017).*
United States Patent Office Notice of Allowance for U.S. Appl. No. 16/608,140 dated Sep. 11, 2020 (13 pages).
Gupta et al., "Animal Models for Heart Failure," Methods in Molecular Medicine, vol. 129: Cardiovascular Disease: Methods and Protocols, vol. 2: Molecular Medicine Edited by: Q. K. Wang, Humana Press Inc., Totowa, NJ, 2007, pp. 97-114.
Schreckenberg et al., "Calcium sensing receptor expression and signalling in cardiovascular physiology and disease," Vascular Pharmacology 107 (2018) 35-42.
Jones et al., "Regulation of Ca2+ signaling in transgenic mouse cardiac myocytes overexpressing calsequestrin," J Clin Invest. 1998, 101(7):1385-1393.
Wang et al., "Murine models for the study of congestive heart failure: Implications for understanding molecular mechanisms and for drug discovery," Journal of Pharmacological and Toxicological Methods 50 (2004) 163-174.
Chinese Patent Office Action for Application No. 201680076074.0 dated Apr. 13, 2020 (14 pages, English translation included).
European Patent Office Extended Search Report for Application No. 17774891.0 dated Oct. 29, 2019 (7 pages).
Yamamura et al., "Inhibition of Excessive Cell Proliferation by Calcilytics in Idiopathic Pulmonary Arterial Hypertension," PLoS ONE, 2015, 10(9):e0138384 (16 pages).
Brunner et al., "The cardioprotective effects of parathyroid hormone are independent of endogenous granulocyte-colony stimulating factor release," Cardiovascular Research, 2012, 93:330-339.
Cha et al., "Parathyroid hormone accelerates decompensation following left ventricular hypertrophy," Experimental and Molecular Medicine, 2010, 42(1):61-68.
Li et al., "Role of Calcium-Sensing Receptor in Cardiac Injury of Hereditary Epileptic Rats," Pharmacology, 2015, 95:10-21.
Liu et al., "Calhex231 Ameliorates Cardiac Hypertrophy by Inhibiting Cellular Autophagy in Vivo and in Vitro," Cell Physiol Biochem, 2015, 36:1597-1612.
Liu et al., "Rat Parathyroid Hormone 1—34 Signals through the MEK/ERK Pathway to Induce Cardiac Hypertrophy," The Journal of International Medical Research, 2008, 36:942-950.

(Continued)

*Primary Examiner* — Shirley V Gembeh
(74) *Attorney, Agent, or Firm* — Michael Best & Friedrich LLP

(57) ABSTRACT

An object of the present invention is to provide a medicament for preventing or treating pulmonary hypertension. The present invention provides a medicament for preventing or treating pulmonary hypertension, comprising a compound selected from the group consisting of (5R)-N-[1-ethyl-1-(4-ethylphenyl)propyl]-2,7,7-trimethyl-5-phenyl-4,5,6,7-tetrahydropyrazolo[1,5-a]pyrimidine-3-carboxamide, (5R)-N-[1-ethyl-1-(4-methoxyphenyl)propyl]-2,7,7-trimethyl-5-phenyl-4,5,6,7-tetrahydropyrazolo[1,5-a]pyrimidine-3-carboxamide, (5R)-N-[1-ethyl-1-(4-ethylphenyl)propyl]-5-(2-fluorophenyl)-2,7,7-trimethyl-4,5,6,7-tetrahydropyrazolo[1,5-a]pyrimidine-3-carboxamide, and the salt thereof.

2 Claims, 1 Drawing Sheet

(56) References Cited

OTHER PUBLICATIONS

Lu et al., "Role of the Calcium-Sensing Receptor in Cardiomyocyte Apoptosis via the Sarcoplasmic Reticulum and Mitochondrial Death Pathway in Cardiac Hypertrophy and Heart Failure," Cell Physiol Biochem, 2013, 31:728-743.
Smogorzewski et al., "Parathyroid hormone increases cytosolic calcium concentration in adult rat cardiac myocytes," Am J Physiol Heart Circ Physiol, 1993, 264:H1998-H2006.
Sun et al., "Calcium-sensing receptor: a sensor and mediator of ischemic preconditioning in the heart," Am J Physiol, Heart Cir Physiol, 2010, 299:H1309-H1317.
Tastan et al., "Parathyroid hormone improves contractile performance of adult rat ventricular cardiomyocytes at low concentrations in a non-acute way," Cardiovascular Research, 2009, 82:77-83.
Tfelt-Hansen et al., "Calcium receptor is functionally expressed in rat neonatal ventricular cardiomyocytes," Am J Physiol Heart Circ Physiol, 2006, 290:H1165-H1171.
Yoshida et al., "Discovery of Novel and Potent Orally Active Calcium-Sensing Receptor Antagonists that Stimulate Pulselike Parathyroid Horone Secretion: Synthesis and Structure—Activity Relationships of Tetrahydropyrazolopyrimidine Derivates," J Med Chem, 2011, 54(5):1430-1440.
Yoshida et al., "Synthesis and structure-activity relationship of tetrahydropyrazolopyrimidine derivatives—A novel structural class of potent calcium-sensing receptor antagonists," Bioorg Med Chem, 2010, 18(24):8501-8511.
Zaruba et al., Parathyroid hormone treatment after myocardial infarction promotes cardiac repair by enhanced neovascularization and cell survival, Cardiovascular Research, 2008, 77:722-731.
Zhang et al., "Calcium Sensing Receptor Promotes Cardiac Fibroblast Proliferation and Extracellular Matrix Secretion," Cell Physiol Biochem, 2014, 33:557-568.
European Patent Office Extended Search Report for Application No. 16878768.7 dated Aug. 5, 2019 (8 pages).
International Search Report for Application No. PCT/JP2018/016995 dated Jun. 12, 2018 (4 pages).
International Search Report for Application No. PCT/JP2018/016996 dated Jun. 19, 2018 (4 pages).
International Search Report for Application No. PCT/JP2016/088121 dated Mar. 14, 2017 (5 pages).
International Search Report for Application No. PCT/JP2017/012305 dated May 16, 2017 (8 pages).
Written Opinion for Application No. PCT/JP2017/012305 dated May 16, 2017 (8 pages).
Guo et al., "Inhibition of the Ca2+-sensing receptor rescues pulmonary hypertension in rats and mice," Hypertension Research, 2014, 37(2):116-124.
Schepelmann et al., "The vascular Ca2+-sensing receptor regulates blood vessel tone and blood pressure," Am J Physiol Cell Physiol, 2016, 310:C193—C204.
Tang, H. et al., "Pathogenic role of calcium-sensing receptors in the development and progression of pulmonary hypertension," Am. J. Physiol. Lung Cell Mol. Physiol., 2016, 310(5):L846-L859.
Yamamura et al., "Calcilytics enhance sildenafil-induced antiproliferation in idiopathic pulmonary arterial hypertension," European Journal of Pharmacology, 2016, 784:15-21.
Yamamura et al., "Dihydropyridine Ca2+ Channel Blockers Increase Cytosolic [Ca2+] by Activating Ca2+-sensing Receptors in Pulmonary Arterial Smooth Muscle Cells," Circulation Research, 2013, 112(4):640-650.
"Yamamura et al., "Enhanced Ca2+-Sensing Receptor Function in Idiopathic Pulmonary Arterial Hypertension," Circulation Research, 2012, 111(4):469-481."
Yamamura et al., "Enhanced Ca2+-sensing Receptor Function in Pulmonary Hypertension", Journal of the Pharmaceutical Society of Japan, 2013, 133(12):1351-1359.
Yamamura et al., "Pathological function of Ca2+-sensing receptor in pulmonary arterial hypertension," J. Smooth Muscle Res., 2014, 50:8-17.
"Yoshida, M. et al., "Novel and potent calcium-sensing receptor antagonists: Discovery of (5R)-N-[1-ethyl-1-(4-ethylphenyl)propyl]-2,7,7-trimethyl-5-phenyl-4,5,6,7-tetrahydropyrazolo [I,5-a]pyrimidine-3-carboxamide monotosylate (TAK-075) as an orally active bone anabolic agent," Bioorganic & Medicinal Chemistry, 2011, 19(6):1881-1894."

* cited by examiner

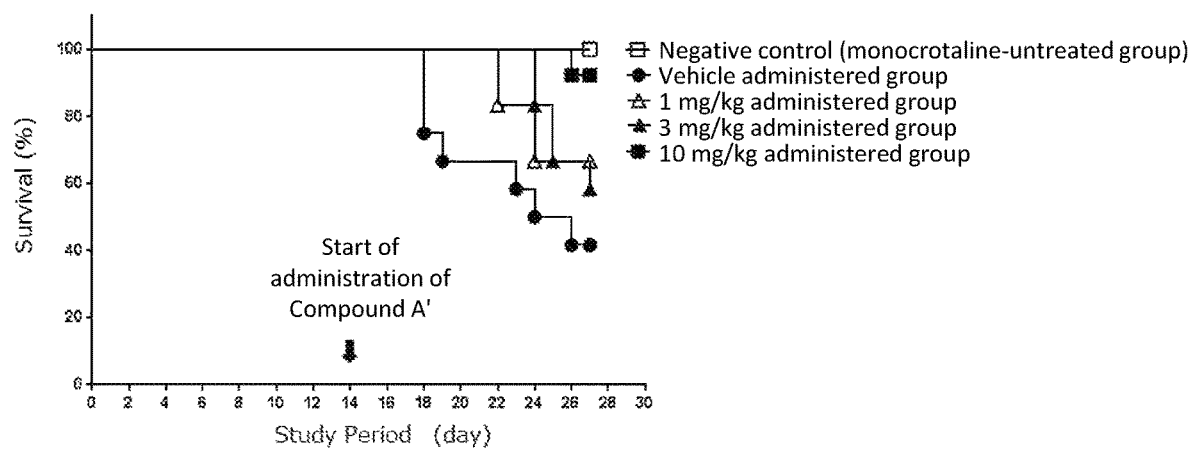
Effect on survival in monocrotaline-induced pulmonary hypertensive rat models

MEDICAMENT

CROSS-REFERENCE TO RELATED APPLICATION(S)

This is a U.S. national stage entry of International Patent Application No. PCT/JP2017/012305, filed on Mar. 27, 2017, which claims priority to Japanese Patent Application No. 2016-063747, filed on Mar. 28, 2016, the entire contents of each of which are fully incorporated herein by reference.

TECHNICAL FIELD

The present invention relates to a medicament for preventing or treating pulmonary hypertension.

BACKGROUND ART

Pulmonary hypertension is an increase of pulmonary artery pressure caused by abnormal proliferation, remodeling, contraction, etc., of myocardial or pulmonary vascular tissues, which is accompanied by right heart failure with the progression of the disease, leading to death. This disease has a very poor prognosis. Main therapeutic drugs currently used are endothelin receptor antagonists, phosphodiesterase 5 inhibitors, prostacyclin analogs, soluble guanylate cyclase (sGC) stimulators, and the like. Although these therapeutic drugs ameliorate some of symptoms, the prognosis of the disease is still poor. In recent years, a plurality of molecules have been found to participate in the pathological condition of the disease. In addition, the existing therapeutic drugs are limited by their effects when used alone. Therefore, the development of a novel therapeutic drug has been demanded.

A calcium-sensing receptor (CaSR) is a G protein-coupled receptor (GPCR) that senses change in extracellular calcium concentration, and is known to be associated with various diseases. Recent reports state that: CaSR is overexpressed in pulmonary artery smooth muscle cells (PASMCs) isolated from pulmonary hypertension patients; and the enhanced functions of CaSR cause abnormal proliferation of pulmonary vascular tissues, etc. In monocrotaline (MCT)-induced pulmonary hypertensive rats and hypoxia-induced pulmonary hypertensive (HPH) mice, a compound NPS-2143 having an effect as a CaSR antagonist has been reported to inhibit cardiac hypertrophy, a rise in right ventricular systolic pressure, myocardial tissue fibrosis, and pulmonary vascular remodeling, etc. (Non Patent Literatures 1 to 5). Also, NPS-2143 and Calhex 231 (negative allosteric modulators) have been reported to enhance the effect of an existing pulmonary arterial hypertension (PAH) drug (PDE 5 inhibitor/sildenafil) (Non Patent Literature 7), and there is a report on the action of CaSR on vascular tone, cardiovascular blood pressure, and pulmonary hypertension using CaSR knockout mice (Non Patent Literatures 8 to 9). However, the medical needs of therapeutic drugs for pulmonary hypertension are still high. Thus, there has been a demand for the development of a medicament for preventing or treating pulmonary hypertension, having excellent properties in terms of drug efficacy, specificity, and low toxicity.

(5R)-N-[1-Ethyl-1-(4-ethylphenyl)propyl]-2,7,7-trimethyl-5-phenyl-4,5,6,7-tetrahydropyrazolo[1,5-a]pyrimidine-3-carboxamide (hereinafter, also referred to as "compound A"), (5R)-N-[1-ethyl-1-(4-methoxyphenyl)propyl]-2,7,7-trimethyl-5-phenyl-4,5,6,7-tetrahydropyrazolo[1,5-a]pyrimidine-3-carboxamide (hereinafter, also referred to as "compound B"), and (5R)-N-[1-ethyl-1-(4-ethylphenyl)propyl]-5-(2-fluorophenyl)-2,7,7-trimethyl-4,5,6,7-tetrahydropyrazolo[1,5-a]pyrimidine-3-carboxamide (hereinafter, also referred to as "compound C") are known to participate in the activity modulation of a calcium-sensing receptor (CaSR) and to participate in the regulation of parathyroid hormone (PTH) (Patent Literatures 1 and 2). Non Patent Literature 6 discloses that tosylate of compound A is a CaSR antagonist.

CITATION LIST

Patent Literature

Patent Literature 1: WO2004/017908
Patent Literature 2: Japanese Patent Laid-Open No. 2005-239611

Non Patent Literature

Non Patent Literature 1: Circ. Res., 111 (4): 469-481, 2012
Non Patent Literature 2: Circ. Res., 112 (4): 640-650, 2013
Non Patent Literature 3: YAKUGAKU ZASSHI, 133 (12): 1351-1359, 2013
Non Patent Literature 4: J. Smooth Muscle Res., 50: 8-17, 2014
Non Patent Literature 5: Hypertens Res., 37 (2): 116-124, 2014
Non Patent Literature 6: Bioorganic & Medicinal Chemistry 19: 1881-1894, 2011
Non Patent Literature 7: Eur. J. Pharmacol. 784: 15-21, 2016
Non Patent Literature 8: Am. J. Physiol. Lung Cell Mol. Physiol. 310: 846-859, 2016
Non Patent Literature 9: Am. J. Physiol. Cell Physiol. 310: 193-204, 2016

SUMMARY OF INVENTION

Technical Problem

The present invention provides a medicament for preventing or treating pulmonary hypertension.

Solution to Problem

The present inventors have found that a compound selected from the group consisting of compound A, compound B, compound C, and the salt thereof is effective for preventing or treating pulmonary hypertension. The present invention has been made on the basis of this finding.

Specifically, the present invention provides the following aspects:

[1] A medicament for preventing or treating pulmonary hypertension, comprising a compound selected from the group consisting of (5R)-N-[1-ethyl-1-(4-ethylphenyl)propyl]-2,7,7-trimethyl-5-phenyl-4,5,6,7-tetrahydropyrazolo[1,5-a]pyrimidine-3-carboxamide, (5R)-N-[1-ethyl-1-(4-methoxyphenyl)propyl]-2,7,7-trimethyl-5-phenyl-4,5,6,7-tetrahydropyrazolo[1,5-a]pyrimidine-3-carboxamide, (5R)-N-[1-ethyl-1-(4-ethylphenyl)propyl]-5-(2-fluorophenyl)-2,7,7-trimethyl-4,5,6,7-tetrahydropyrazolo[1,5-a]pyrimidine-3-carboxamide, and the salt thereof.

[2] The medicament according to [1], wherein the pulmonary hypertension is pulmonary arterial hypertension.

[3] A method of preventing or treating pulmonary hypertension in a mammal, comprising administering to the mammal a compound selected from the group consisting of (5R)-N-[1-ethyl-1-(4-ethylphenyl)propyl]-2,7,7-trimethyl-5-phenyl-4,5,6,7-tetrahydropyrazolo[1,5-a]pyrimidine-3-carboxamide, (5R)-N-[1-ethyl-1-(4-methoxyphenyl)propyl]-2,7,7-trimethyl-5-phenyl-4,5,6,7-tetrahydropyrazolo[1,5-a]pyrimidine-3-carboxamide, (5R)-N-[1-ethyl-1-(4-ethylphenyl)propyl]-5-(2-fluorophenyl)-2,7,7-trimethyl-4,5,6,7-tetrahydropyrazolo[1,5-a]pyrimidine-3-carboxamide, and the salt thereof.

[4] The method according to [3], wherein the pulmonary hypertension is pulmonary arterial hypertension.

[5] A compound selected from the group consisting of (5R)-N-[1-ethyl-1-(4-ethylphenyl)propyl]-2,7,7-trimethyl-5-phenyl-4,5,6,7-tetrahydropyrazolo[1,5-a]pyrimidine-3-carboxamide, (5R)-N-[1-ethyl-1-(4-methoxyphenyl)propyl]-2,7,7-trimethyl-5-phenyl-4,5,6,7-tetrahydropyrazolo[1,5-a]pyrimidine-3-carboxamide, (5R)-N-[1-ethyl-1-(4-ethylphenyl)propyl]-5-(2-fluorophenyl)-2,7,7-trimethyl-4,5,6,7-tetrahydropyrazolo[1,5-a]pyrimidine-3-carboxamide, and the salt thereof, for preventing or treating pulmonary hypertension.

[6] The compound according to [5], wherein the pulmonary hypertension is pulmonary arterial hypertension.

[7] Use of a compound selected from the group consisting of (5R)-N-[1-ethyl-1-(4-ethylphenyl)propyl]-2,7,7-trimethyl-5-phenyl-4,5,6,7-tetrahydropyrazolo[1,5-a]pyrimidine-3-carboxamide, (5R)-N-[1-ethyl-1-(4-methoxyphenyl)propyl]-2,7,7-trimethyl-5-phenyl-4,5,6,7-tetrahydropyrazolo[1,5-a]pyrimidine-3-carboxamide, (5R)-N-[1-ethyl-1-(4-ethylphenyl)propyl]-5-(2-fluorophenyl)-2,7,7-trimethyl-4,5,6,7-tetrahydropyrazolo[1,5-a]pyrimidine-3-carboxamide, and the salt thereof for manufacturing a preventive or treatment agent for pulmonary hypertension.

The use according to [7], wherein the pulmonary hypertension is pulmonary arterial hypertension.

Advantageous Effects of Invention

According to the present invention, pulmonary hypertension can be prevented or treated. The medicament of the present invention can be orally administered, and when orally administered, produces fewer adverse reactions (e.g., infection) as compared with a medicament for non-oral administration. The medicament of the present invention is expected to have an excellent therapeutic effect and prognosis-improving effect on pulmonary hypertension, and furthermore, is advantageously easily handled by patients, healthcare professionals, and persons involved.

BRIEF DESCRIPTION OF DRAWING

FIG. 1 shows a Kaplan-Meier survival curve of each administration group in monocrotaline-induced pulmonary hypertensive rat models.

DESCRIPTION OF EMBODIMENTS

In the present specification, the term "subject" refers to a mammal, for example, a human. In the present specification, the "subject having pulmonary hypertension" means a subject affected by pulmonary hypertension. When the subject is a human, the subject is called a "patient". When the subject affected by pulmonary hypertension is a human, the subject is called a "pulmonary hypertension patient".

In the present specification, the term "pharmaceutically acceptable salt" means an acid-addition salt or a base-addition salt that is acceptable for administration to organisms.

In the present specification, the term "therapeutically effective amount" means an amount which results in a therapeutic effect on the subject, and means, for example, that in the subject who has received the amount, the symptom of the disease or condition is alleviated, mitigated, or the development of the symptom of the disease or condition is delayed or inhibited compared with a subject who has not received the amount. A therapeutically effective amount can be appropriately determined by doctors in view of the age, weight, sex and the severity of the disease of the subject.

In the present specification, the term "pulmonary hypertension" means a condition in which pulmonary artery pressure is increased. General "hypertension" means a condition in which the pressure within a vascular vessel of blood sent from the left ventricle through the aorta into the body is elevated. By contrast, the "pulmonary hypertension" is a condition in which the pulmonary artery from the right ventricle to the lung has high blood pressure. The pulmonary hypertension occurs independently of the general hypertension. The normal values of pulmonary artery pressure at rest are a systolic pressure of approximately 20 mmHg to approximately 30 mmHg, a diastolic pressure of approximately 7 mmHg to approximately 12 mmHg, and a mean pressure of approximately 10 mmHg to approximately 15 mmHg in the human lung.

Diagnostic criteria for pulmonary hypertension are described in, for example, the Guidelines for treatment of pulmonary hypertension (2012, revised) provided by The Japanese Circulation Society.

The diagnosis of pulmonary hypertension in humans is usually conducted on the basis of mean pulmonary artery pressure (mean PAP) actually measured by right heart catheterization at rest. A subject having a mean pulmonary artery pressure of 25 mmHg or higher can be diagnosed as having pulmonary hypertension. Recent advances of echocardiography allow pulmonary artery pressure to be estimated in a non-invasive manner. The diagnosis of pulmonary hypertension is also conducted on the basis of the estimated value of pulmonary artery pressure.

The pulmonary hypertension is clinically classified according to the Dana Point classification into five groups: group 1 to group 5. Group 1 is pulmonary arterial hypertension (PAH); group 2 is pulmonary hypertension owing to left ventricular cardiac disease; group 3 is pulmonary hypertension owing to lung diseases and/or hypoxia; group 4 is chronic thromboembolic pulmonary hypertension; and group 5 is pulmonary hypertension with unclear multifactorial mechanisms. Group 1' (pulmonary veno-occlusive disease and/or pulmonary capillary hemangiomatosis) and group 1" (persistent pulmonary hypertension of the newborn) are also known as subgroups of group 1.

The pulmonary arterial hypertension of group 1 is the most typical pulmonary hypertension and is broadly divided into idiopathic PAH, heritable PAH, drug- and toxin-induced PAH, and PAH owing to each disease.

In the present invention, various symptoms associated with pulmonary hypertension (e.g., elevated right ventricular pressure) can be improved (for example, pulmonary artery pressure in a subject can be lowered) by the administration of a compound selected from the group consisting of compounds A, B, and C, and the salt thereof to the subject.

Thus, the present invention provides a medicament for preventing or treating pulmonary hypertension, comprising a compound selected from compounds A, B, and C, and the salt thereof.

Compound A is represented by the following formula:

[Formula 1]

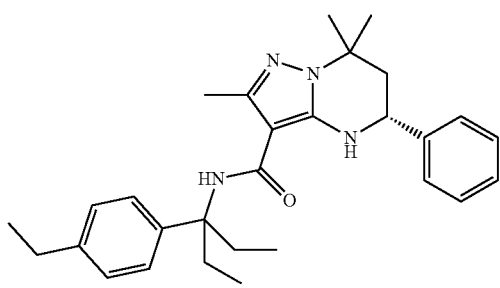

Compound B is represented by the following formula:

[Formula 2]

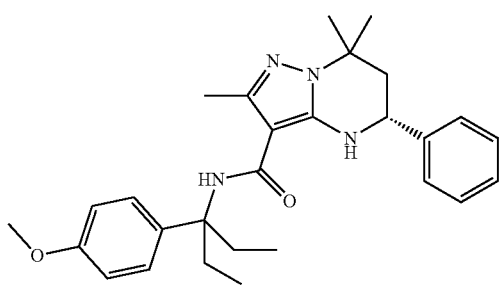

Compound C is represented by the following formula:

[Formula 3]

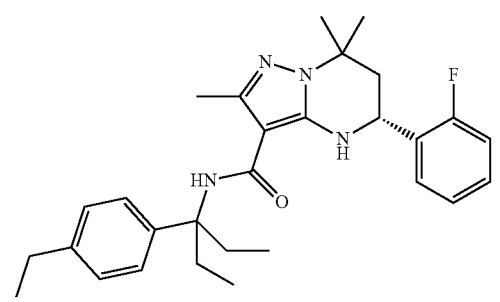

In a particular aspect of the present invention, the medicament of the present invention can be used in the prevention or treatment of pulmonary hypertension selected from the following pulmonary hypertensions: pulmonary artery hypertension; pulmonary hypertension caused by pulmonary veno-occlusive disease, and pulmonary hypertension caused by pulmonary capillary hemangiomatosis; persistent pulmonary hypertension of the newborn; pulmonary hypertension accompanied by left ventricular systolic dysfunction, left ventricular diastolic dysfunction, valvular disease, or congenital or acquired left ventricular inflow or outflow tract obstruction; pulmonary hypertension caused by chronic obstructive lung disease, interstitial lung disease, other lung diseases accompanied by mixed restrictive and obstructive disorder, sleep-disordered breathing, alveolar hypoventilation syndrome, chronic exposure to high altitude, or disturbance of development; chronic thromboembolic pulmonary hypertension; and pulmonary hypertension accompanied by hematologic disorders (chronic hemolytic anemia, myeloproliferative disease, or splenectomy), systemic disorders (sarcoidosis, pulmonary Langerhans' cell histiocytosis, lymphangioleiomyomatosis, neurofibromatosis, or vasculitis), metabolic disorders (glycogenosis, Gaucher's disease, or thyroid gland disease), or other vascular compressions of the lung (tumor embolism, fibrous mediastinitis, or chronic renal failure). The medicament of the present invention can preferably be used in the prevention or treatment of pulmonary arterial hypertension.

Compound A, B, or C, or the salt thereof may be a non-solvate or may be a solvate. The solvate can be formed in a solvent such as ethanol or water. The solvate whose solvent is water is a hydrate. The hydrate encompasses stoichiometric hydrates as well as hydrates containing various amounts of water.

Compound A, B, or C, or the salt thereof may be labeled with an isotope (e.g., $^{3}H$, $^{13}C$, $^{14}C$, $^{18}F$, $^{35}S$, and $^{125}I$) or the like.

A deuterium conversion form having $^{2}H(D)$ converted from $^{1}H$ is also included in compound A, B, or C, or the salt thereof.

Examples of the salt of compound A, B, or C include salts with inorganic bases, ammonium salts, salts with organic bases, salts with inorganic acids, salts with organic acids, and salts with basic or acidic amino acids.

Preferred examples of the salts with inorganic bases include: alkali metal salts such as sodium salt and potassium salt; alkaline earth metal salts such as calcium salt, magnesium salt, and barium salt; and aluminum salts.

Preferred examples of the salts with organic bases include salts with trimethylamine, triethylamine, pyridine, picoline, ethanolamine, diethanolamine, triethanolamine, dicyclohexylamine, and N,N'-dibenzylethylenediamine.

Preferred examples of the salts with inorganic acids include salts with hydrochloric acid, hydrobromic acid, nitric acid, sulfuric acid, and phosphoric acid.

Preferred examples of the salts with organic acids include salts with formic acid, acetic acid, trifluoroacetic acid, fumaric acid, oxalic acid, tartaric acid, maleic acid, citric acid, succinic acid, malic acid, methanesulfonic acid, benzenesulfonic acid, and p-toluenesulfonic acid.

Preferred examples of the salts with basic amino acids include salts with arginine, lysine, and ornithine.

Preferred examples of the salts with acidic amino acids include salts with aspartic acid and glutamic acid.

Among these salts, a pharmaceutically acceptable salt is preferred.

In a particular aspect of the present invention, the salt of compound A can be p-toluenesulfonate (tosylate) (hereinafter, also referred to as "compound A'"). In a particular aspect of the present invention, the salt of compound B can be hydrochloride (hereinafter, also referred to as "compound B'"). In a particular aspect of the present invention, the salt of compound C can be p-toluenesulfonate (tosylate) (hereinafter, also referred to as "compound C'").

In a particular aspect of the present invention, a compound selected from compound A, compound A', compound B, compound B', compound C, and compound C' can be used in the prevention or treatment of pulmonary hypertension. Thus, the present invention provides a medicament for preventing or treating pulmonary hypertension, comprising a compound selected from compound A, compound A', compound B, compound B', compound C, and compound C'. In this particular aspect, the pulmonary hypertension can be pulmonary arterial hypertension.

In a particular aspect of the present invention, compound A or compound A' can be used in the prevention or treatment of pulmonary hypertension. Thus, the present invention provides a medicament for preventing or treating pulmonary hypertension, comprising compound A or compound A'. In this particular aspect, the pulmonary hypertension can be pulmonary arterial hypertension.

In a particular aspect of the present invention, compound A' can be used in the prevention or treatment of pulmonary hypertension. Thus, the present invention provides a medicament for preventing or treating pulmonary hypertension, comprising compound A'. In this particular aspect, the pulmonary hypertension can be pulmonary arterial hypertension.

In a particular aspect of the present invention, the present invention further provides a medicament for improving one or more conditions selected from the group consisting of right ventricular pressure, right ventricular systolic pressure, a survival rate, and cardiac hypertrophy in a subject having pulmonary hypertension, comprising a compound selected form compounds A, B, and C, and the salt thereof.

In a particular aspect of the present invention, the present invention provides a medicament for improving one or more conditions selected from the group consisting of right ventricular pressure, right ventricular systolic pressure, a survival rate, and cardiomegaly in a subject having pulmonary hypertension, comprising compound A or a salt of compound A.

In a particular aspect of the present invention, the present invention provides a medicament for improving one or more conditions selected from the group consisting of right ventricular pressure, right ventricular systolic pressure, a survival rate, and cardiomegaly in a subject having pulmonary hypertension, comprising compound A'.

Compounds A, B, and C, and the salt thereof can be prepared by a method known per se in the art (e.g., a method described in WO2004/017908 and Yoshida M. et al., Bioorg. Med. Chem., 19: 1881-1894, 2011).

The dose differs depending on a recipient subject, an administration route, a disease, symptoms, etc. In the case of, for example, oral administration to a human (body weight: approximately 50 kg), the dose can be selected from the range of approximately 0.1 mg to approximately 500 mg, preferably the range of approximately 1 mg to approximately 100 mg, in terms of the amount of compound A, B, or C. In the case of non-oral administration to a human (body weight: approximately 50 kg), the dose can be selected from the range of approximately 0.01 mg to approximately 100 mg, preferably the range of approximately 0.1 mg to approximately 10 mg, in terms of the amount of compound A, B, or C. This amount can be administered in one portion to several divided portions per day (e.g., one portion to three portions per day).

The medicament of the present invention may contain a pharmaceutically acceptable carrier in addition to the compound selected from compounds A, B, and C, and the salt thereof.

Any of various organic or inorganic carrier materials routinely used as pharmaceutical materials may be used as the pharmaceutically acceptable carrier and may be mixed as excipients, lubricants, binding agents, and disintegrants for solid preparations; and solvents, solubilizing agents, suspending agents, isotonic agents, buffering agents, and soothing agents for liquid preparations. If necessary, pharmaceutical additives such as preservatives, antioxidants, stabilizers, colorants, and sweeteners can also be used.

In a certain aspect, the medicament of the present invention can be a medicament for parenteral administration or for oral administration. The medicament of the present invention can also be a medicament for oral administration.

The medicament of the present invention can be used in combination with a drug such as a different therapeutic drug for pulmonary hypertension and can be used in combination with, for example, any of the following drugs:

(1) Endothelin Receptor Antagonists

Endothelin receptor antagonists such as macitentan, bosentan, and ambrisentan (2) Prostaglandin Preparations Prostaglandin preparations (or prostacyclin preparations) such as epoprostenol, beraprost, treprostinil, iloprost, and selexipag (3) Phosphodiesterase-5 Inhibitors Phosphodiesterase-5 inhibitors such as sildenafil and tadalafil (4) Soluble Adenylate Cyclase Stimulators Soluble adenylate cyclase stimulators such as riociguat (5) Calcium Channel Blockers Calcium channel blockers such as nifedipine, diltiazem, and amlodipine (6) Rho Kinase Inhibitors Rho kinase inhibitors such as fasudil (7) Others Tyrosine kinase inhibitors such as imatinib and sorafenib; anticoagulants such as warfarin and aspirin; diuretics such as furosemide and spironolactone; cardiotonics such as dopamine and digoxin; etc.

The medicament mixed with or used in combination with the medicament of the present invention includes all of a medicament formulated as a single preparation containing the compound selected from compounds A, B, and C, and the salt thereof and the concomitant drug; and separate preparations of the compound selected from compounds A, B, and C, and the salt thereof and the concomitant drug. Hereinafter, these preparations are collectively referred to as the combined use agent of the present invention.

The combined use agent of the present invention can be prepared by separately or simultaneously formulating the compound selected from compounds A, B, and C, and the salt thereof and the concomitant drug, either directly or after mixing with a pharmaceutically acceptable carrier, etc., in the same way as in the aforementioned medicament comprising the compound selected from compounds A, B, and C, and the salt thereof. The daily dose of the combined use agent of the present invention differs depending on severity of the condition; the age, sex, body weight, and difference in sensitivity of a recipient subject; the time of administration and dosing intervals; the properties, prescription, or type of the medicament; the type of the active ingredient, etc., and is not particularly limited.

For the administration of the combined use agent of the present invention, the compound selected from compounds A, B, and C, and the salt thereof and the concomitant drug may be administered at the same time. Alternatively, the concomitant drug may be first administered, followed by the administration of the compound selected from compounds A, B, and C, and the salt thereof, or the compound selected from compounds A, B, and C, and the salt thereof may be first administered, followed by the administration of the concomitant drug. In the case of administering the compound and the concomitant drug in the staggered manner, the time interval differs depending on the active ingredient to be administered, the dosage form, and the administration method. Examples of the method for first administering the concomitant drug include a method which involves administering the concomitant drug and administering the compound selected from compounds A, B, and C, and the salt thereof within 1 minute to 3 days, preferably within 10 minutes to 1 day, more preferably within 15 minutes to 1 hour thereafter. Examples of the method for first administering the compound selected from compounds A, B, and C, and the salt thereof include a method which involves administering the compound and administering the concomitant drug within 1 minute to 1 day, preferably within 10 minutes to 6 hours, more preferably within 15 minutes to 1 hour thereafter.

The respective amounts of the compound selected from compounds A, B, and C, and the salt thereof and the concomitant drug in the combined use agent of the present invention containing the compound selected from compounds A, B, and C, and the salt thereof and the concomitant drug in a single preparation differ depending on the form of the preparation and are usually approximately 0.01 to 90% by weight, preferably approximately 0.1 to 50% by weight, more preferably approximately 0.5 to 20% by weight, with respect to the total weight of the preparation.

The content of the carrier in the combined use agent is usually approximately 0 to 99.8% by weight, preferably approximately 10 to 99.8% by weight, more preferably approximately 10 to 90% by weight, with respect to the total weight of the preparation.

When the combined use agent of the present invention comprises separate medicaments respectively containing the compound selected from compounds A, B, and C, and the salt thereof and the concomitant drug, the combined use agent containing the concomitant drug can be produced in the same way as in the combined use agent comprising the compound selected from compounds A, B, and C, and the salt thereof.

The medicament of the present invention may be any of solid preparations including powders, granules, tablets, and capsules, and liquid preparations including syrups and emulsions.

The medicament of the present invention can be produced by a routine method, for example, mixing, kneading, granulation, tableting, coating, sterilization, and/or emulsification, according to the form of the preparation. For such pharmaceutical production, see, for example, each section of the Japanese Pharmacopoeia (16th edition) General Rules for Preparations. The medicament of the present invention may be prepared into a sustained-release agent containing the active ingredient and a biodegradable polymer compound.

In a certain aspect of the present invention, the present invention provides a medicament for preventing or treating pulmonary hypertension in a subject in need thereof, comprising a compound selected from compounds A, B, and C, and the salt thereof, wherein the compound is used in combination with a concomitant drug.

In an alternative aspect of the present invention, the present invention provides a method for preventing or treating pulmonary hypertension in a subject in need thereof, comprising administering a compound selected from compounds A, B, and C, and the salt thereof to the subject. In the method of the present invention, the pulmonary hypertension to be treated can be any of the diseases and the conditions described as the subject to be treated as to the medicament of the present invention. In the present method, a therapeutically effective amount of said compound can be administered to the subject. In the case of administering the compound selected from compounds A, B, and C, and the salt thereof in the method of the present invention, a medicament comprising the compound selected from compounds A, B, and C, and the salt thereof may be administered.

In a further alternative aspect of the present invention, the present invention provides use of a compound selected from compounds A, B, and C, and the salt thereof for producing or in the manufacture of a medicament for preventing or treating pulmonary hypertension in a subject in need thereof. The pulmonary hypertension to be treated with the medicament can be any of the diseases and the conditions described as the subject to be treated as to the medicament of the present invention.

In a further aspect of the present invention, the present invention provides a compound selected from the group consisting of compounds A, B, and C, and the salt thereof for use in preventing or treating pulmonary hypertension in a subject in need thereof. The pulmonary hypertension to be treated with the medicament can be any of the diseases and the conditions described as the subject to be treated as to the medicament of the present invention.

In a certain aspect of the present invention, the compound contained in the compound or the medicament to be administered is tosylate salt of compound A.

EXAMPLES

Compound A' was prepared by the known method described in WO2004/017908 and Yoshida M. et al., Bioorg. Med. Chem., 19: 1881-1894, 2011.

Example 1

Therapeutic Effect of Compound A' on Pulmonary Hypertension in Pulmonary Hypertensive Animal Model (Right Ventricular Pressure, Right Ventricular Systolic Pressure, Right Ventricular Hypertrophy, Pulmonary Artery Medial Wall Thickening, Pulmonary Artery Occlusion)

(1) Experimental Method

Monocrotaline (MCT) was subcutaneously injected at 50 mg/kg (in 50% dimethyl sulfoxide solution) to male Sprague-Dawley rats having a body weight of 250 g ± 10% to prepare pulmonary hypertensive rat models. Compound A' and the same amount of a vehicle were orally administered to a compound A' administration group (dose: 1 mg/kg, 3 mg/kg, or 10 mg/kg) and a control group, respectively, every day over 14 days from the 14th day after the MCT administration. This experiment was carried out using these groups each involving 9 rats (12 rats were used only in a vehicle control group).

(2) Effect on Right Ventricular Pressure (RVP)

The right ventricular pressure (RVP) was measured by catheterization for the rats that survived at 28 days after MCT administration (negative control group (monocrotaline non-administered group), 9 rats; vehicle control group, 8 rats; compound A' 1 mg/kg administration group, 9 rats; compound A' 3 mg/kg administration group, 5 rats; compound A' 10 mg/kg administration group, 9 rats; total 40 rats). The results are shown in Table 1.

TABLE 1

Effect on right ventricular pressure (RVP) in monocrotaline-induced pulmonary hypertensive rat model

|  | RVP (mmHg) | SD |
|---|---|---|
| Negative control group (monocrotaline non-administered group) | 12.6 | 3.0 |
| Vehicle control group | 30.4 | 3.5 |
| 1 mg/kg administration group | 26.4 | 3.0 |
| 3 mg/kg administration group | 22.4 | 5.0 |
| 10 mg/kg administration group | 17.8 | 2.4 |

The data in the table is indicated by mean± standard deviation.

As shown in Table 1, compound A' remarkably improved the right ventricular pressure at 28 days after MCT administration.

(3) Effect on Right Ventricular Systolic Pressure (RVSP)

The right ventricular systolic pressure (RVSP) was measured by catheterization for the rats that survived at 28 days after MCT administration ((negative control group (monocrotaline non-administered group), 9 rats; vehicle control group, 8 rats; compound A' 1 mg/kg administration group, 9 rats; compound A' 3 mg/kg administration group, 5 rats; compound A' 10 mg/kg administration group, 9 rats; total 40 rats)). The results are shown in Table 2.

TABLE 2

Effect on right ventricular systolic pressure (RVSP) in monocrotaline-induced pulmonary hypertensive rat model

|  | RVSP (mmHg) | SD |
|---|---|---|
| Negative control group (monocrotaline non-administered group) | 22.2 | 3.2 |
| Vehicle control group | 56.5 | 4.7 |
| 1 mg/kg administration group | 48.3 | 5.3 |
| 3 mg/kg administration group | 39.1 | 2.9 |
| 10 mg/kg administration group | 28.0 | 3.4 |

The data in the table is indicated by mean± standard deviation.

As shown in Table 2, compound A' remarkably improved the right ventricular systolic pressure (RVSP) at 28 days after MCT administration.

(4) Effect on Right Ventricular Hypertrophy

The right ventricle weight (RV), left ventricle weight (LV), and interventricular septum weight (S) were measured for pulmonary hypertensive rat models that survived at 28 days after MCT administration (negative control group (monocrotaline non-administered group), 9 rats; vehicle control group, 8 rats; compound A' 1 mg/kg administration group, 9 rats; compound A' 3 mg/kg administration group, 5 rats; compound A' 10 mg/kg administration group, 9 rats; total 40 rats)), and RV/(LV+S) was determined as an index for right cardiomegaly. The results are shown in Table 3.

TABLE 3

Effect on right ventricular hypertrophy in monocrotaline-induced pulmonary hypertensive rat model

|  | RV/(LV + S) | SD |
|---|---|---|
| Negative control group (monocrotaline non-administered group) | 0.271 | 0.042 |
| Vehicle control group | 0.452 | 0.108 |
| 1 mg/kg administration group | 0.333 | 0.035 |
| 3 mg/kg administration group | 0.307 | 0.062 |
| 10 mg/kg administration group | 0.282 | 0.070 |

The data in the table is indicated by mean± standard deviation.

As shown in Table 3, compound A' remarkably improved the right ventricular hypertrophy at 28 days after MCT administration.

(5) Effect on Pulmonary Artery Medial Wall Thickening

Concerning the pulmonary hypertensive rat models that survived at 28 days after MCT administration (negative control group (monocrotaline non-administered group), 9 rats; vehicle control group, 8 rats; compound A' 10 mg/kg administration group, 9 rats), tissue specimens of pulmonary tissue sections were prepared from 5 rats per group (total 15 rats) by Elastica van Gieson staining method to measure the thickening of the medial wall of the pulmonary artery. The results are shown in Table 4.

TABLE 4

Effect on pulmonary artery medial wall thickening in monocrotaline-induced pulmonary hypertensive rat model

|  | Diameter of pulmonary artery (<50 μM) | | Diameter of pulmonary artery (50 μM-100 μM) | |
|---|---|---|---|---|
|  | Thickness of pulmonary artery medial wall | SE | Thickness of pulmonary artery medial wall | SE |
| Negative control group (monocrotaline non-administered group) | 3.51 | 0.20 | 6.37 | 0.65 |
| Vehicle control group | 5.94 | 0.35 | 12.34 | 0.98 |
| 10 mg/kg administration group | 4.28 | 0.25 | 6.86 | 0.43 |

The data in the table is indicated by mean± standard error.

As shown in Table 4, compound A' remarkably improved the thickening of the pulmonary artery medial wall at 28 days after MCT administration.

(6) Effect on Pulmonary Artery Occlusion

Concerning the pulmonary hypertensive rat models that survived at 28 days after MCT administration (negative control group (monocrotaline non-administered group), 9 rats; vehicle control group, 8 rats; compound A' 10 mg/kg administration group, 9 rats), tissue specimens of pulmonary tissue sections were prepared from 5 rats per group (total 15 rats) by Elastica van Gieson staining method to measure occlusion of the pulmonary artery. A value obtained by dividing a value that is twice as much as the thickness of the pulmonary artery medial wall by the diameter of the pulmonary artery was used as an index of occlusion. The results are shown in Table 5.

TABLE 5

Effect on pulmonary artery occlusion in monocrotaline-
induced pulmonary hypertensive rat model

|  | Diameter of pulmonary artery (<50 μM) | | Diameter of pulmonary artery (50 μM-10 μM) | |
|---|---|---|---|---|
|  | Pulmonary artery occlusion | SE | Pulmonary artery occlusion | SE |
| Negative control group (monocrotaline non-administered group) | 0.19 | 0.01 | 0.19 | 0.02 |
| Vehicle control group | 0.28 | 0.02 | 0.32 | 0.02 |
| 10 mg/kg administration group | 0.20 | 0.01 | 0.19 | 0.01 |

The data in the table is indicated by mean± standard error.

As shown in Table 5, compound A' remarkably improved occlusion of the pulmonary artery at 28 days after MCT administration.

Example 2

Therapeutic Effect of Compound A' on Pulmonary Hypertension in Pulmonary Hypertensive Animal Model (Survival Rate)

(1) Experimental Method

Monocrotaline (MCT) was subcutaneously injected at 50 mg/kg (in 50% dimethyl sulfoxide solution) to male Sprague-Dawley rats having a body weight of 230 g ± 10 g to prepare pulmonary hypertensive rat models. Compound A' and the same amount of a vehicle were orally administered to a compound A' administration group (dose: 1 mg/kg, 3 mg/kg, or 10 mg/kg) and a control group, respectively, once every day over 14 days from the 14th day after the MCT administration. This experiment was carried out using these groups each involving 12 rats.

(2) Effect on Survival Rate

FIG. 1 shows a Kaplan-Meier survival curve obtained from the above experiment.

As shown in FIG. 1, compound A' remarkably improved the survival rate of animals after administration.

Example 3

Effect on CHP1-NHE1 Interaction

In addition to CaSR, NHE ($Na^+$-$H^+$ exchange) protein is shown to be an important molecule involved in the pathology of pulmonary hypertension in experiments or the like involving administration of various NHE inhibitory compounds to animal models of pulmonary hypertension induced by, for example, monocrotaline and hypoxia, as well as NHE knockout animals (Chen et al., 2001; Huetsch et al., 2016; Huetsch and Shimoda, 2015; Yu et al., 2008). CHP is a cofactor essential to the localization of NHE in a cell membrane and the function thereof (Matsushita et al., 2007; Mishima et al., 2007; Pang et al., 2001). Accordingly, whether compound A' inhibits the interaction of NHE1-CHP1 was investigated.

(1) Experimental Method

The inhibitory activity of compound A' on the interaction between human NHE1 and human CHP1 was evaluated in a protein interaction measurement system using an amplified luminescence proximity homogeneous assay (AlphaScreen™ (PerkinElmer)). A microsomal fraction of FLAG-tagged full-length human NHE1 (Accession No. NM 003047) was prepared by being expressed in human embryonic kidney cell-derived FreeStyle™ 293 cells. Also, biotinylated full-length human CHP1 (Accession No. NM 007236) was expressed in a wheat germ cell-free translation system and purified. The NHE1 microsomal fraction and CHP 1 were diluted with an assay buffer (25 mM Tris-HCl (pH 7.4), 137 mM NaCl, 2.7 mM KCl, 0.1% BSA, 1 mM DTT), and compound A' was added thereto. Then, the mixture was added to an Alpha Plate-384 Shallow Well (Perkin Elmer) in an amount of 2 μL/well, and reacted at room temperature for 60 minutes. Acceptor Beads and Donor Beads accompanying an AlphaScreen FLAG(M2) Detection Kit (PerkinElmer) were added thereto each in an amount of 2 μL/well, and the mixture was reacted at room temperature for 60 minutes. Thereafter, the AlphaScreen signal intensity was measured using an EnSpire Multi-label reader (PerkinElmer). Different concentrations of compound A' (concentration: 50.0 nM to 0.8 nM) were evaluated in this test system.

(2) Results

The results are shown in Table 6.

TABLE 6

Effect on CHP1-NHE1 interaction

| Compound | CHP1-NHE1 interaction activity (50% inhibitory concentration) |
|---|---|
| Compound A' | 4.7 nM |

As shown in Table 6, compound A' showed remarkable CHP1-NHE1 inhibitory activity.

INDUSTRIAL APPLICABILITY

The present invention provides a medicament for preventing or treating pulmonary hypertension and is thus useful.

References, such as scientific literatures, patents, and patent applications, cited herein are incorporated herein by reference in their entirety to the same extent as if each individual reference is specifically described.

The present application claims priority to Japanese Patent Application No. 2016-063747 (filed on Mar. 28, 2016), the entire content of which is incorporated herein by reference.

The invention claimed is:

1. A method of treating pulmonary hypertension in a mammal suffering from pulmonary hypertension, comprising
administering to the mammal a compound selected from the group consisting of
(5R)-N-[1-ethyl-1-(4-ethylphenyl)propyl]-2,7,7-trimethyl-5-phenyl-4,5,6,7-tetrahydropyrazolo[1,5-a]pyrimidine-3-carboxamide, and the salt thereof.

2. The method according to claim 1, wherein the pulmonary hypertension is pulmonary arterial hypertension.

* * * * *